US008165460B2

(12) United States Patent
Hickey et al.

(10) Patent No.: US 8,165,460 B2
(45) Date of Patent: Apr. 24, 2012

(54) COATED FILAMENT FOR EVAPORATION/CONDENSATION AEROSOL GENERATION OF THERAPEUTIC AGENTS AND METHODS FOR USING

(75) Inventors: Anthony J. Hickey, Chapel Hill, NC (US); Hugh D. C. Smyth, Albuquerque, NM (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 966 days.

(21) Appl. No.: 11/666,367

(22) PCT Filed: Oct. 26, 2005

(86) PCT No.: PCT/US2005/038713
§ 371 (c)(1),
(2), (4) Date: Apr. 18, 2008

(87) PCT Pub. No.: WO2006/047663
PCT Pub. Date: May 4, 2006

(65) Prior Publication Data
US 2008/0199161 A1    Aug. 21, 2008

Related U.S. Application Data

(60) Provisional application No. 60/622,256, filed on Oct. 26, 2004.

(51) Int. Cl.
*A01G 13/06*    (2006.01)
(52) U.S. Cl. ........ 392/387; 392/386; 392/390; 239/135; 239/136; 239/13

(58) Field of Classification Search .................. 392/386, 392/387, 390; 239/13, 135, 136
See application file for complete search history.

(56) References Cited

U.S. PATENT DOCUMENTS

| | | | |
|---|---|---|---|
| 4,627,432 A | 12/1986 | Newell et al. | |
| 4,811,731 A | 3/1989 | Newell et al. | |
| 4,922,901 A * | 5/1990 | Brooks et al. | ............ 128/203.26 |
| 5,743,251 A | 4/1998 | Howell et al. | |
| 5,823,178 A | 10/1998 | Lloyd et al. | |
| 2004/0091541 A1 | 5/2004 | Unger | |

OTHER PUBLICATIONS

International Search Report and Written Opinion dated May 16, 2006.
International Preliminary Report on Patentability dated May 10, 2007.

(Continued)

*Primary Examiner* — Thor Campbell
(74) *Attorney, Agent, or Firm* — Jenkins, Wilson, Taylor & Hunt, P.A.

(57) ABSTRACT

An apparatus for generating an aerosol of a therapeutic agent and methods of using the same are disclosed. The apparatus comprises a heating element having a surface and a composition coating at least a portion of the heating element surface. The composition comprises a carrier and a therapeutic agent, wherein when the heating element surface is heated to at least the vaporization point of the carrier, the carrier vaporizes and releases the therapeutic agent from the composition as an aerosol. The heating element can be a coiled filament. The therapeutic agent can be a small molecule, a polynucleotide, a polypeptide, or a recombinant virus. The apparatus can be incorporated into a delivery device, such as a metered dose inhaler or an exposure chamber.

56 Claims, 6 Drawing Sheets

OTHER PUBLICATIONS

Crowder TM, Louey MD, Sethuraman VV, Smyth HDC, Hickey AJ (2001) "2001: An Odyssey in Inhaler Formulations And Design," *Pharmaceutical Technology*, 25(7), 99-113.

Smyth HDC, Hickey AJ (2003) "Multimodal Particle Size Distributions Emitted From HFA-134a Solution Pressurized Metered-Dose Inhalers," *AAPS PharmSciTech*, 4(3), Article 38.

Smyth, HDC: (2003) "The Influence Of Formulation Variables On The Performance Of Alternative Propellant-Driven Metered Dose Inhalers," *Advanced Drug Delivery Reviews*, 55(7), 807-828.

Smyth, HDC, Beck VP, Williams D, Hickey AJ (2004) "The Influence Of Formulation And Spacer Device On The In Vitro Performance of Solution Chlorofluorocarbon-Free Propellant-Driven Metered Dose Inhalers," *AAPS PharmSciTech*, 5(1) Article 7.

* cited by examiner

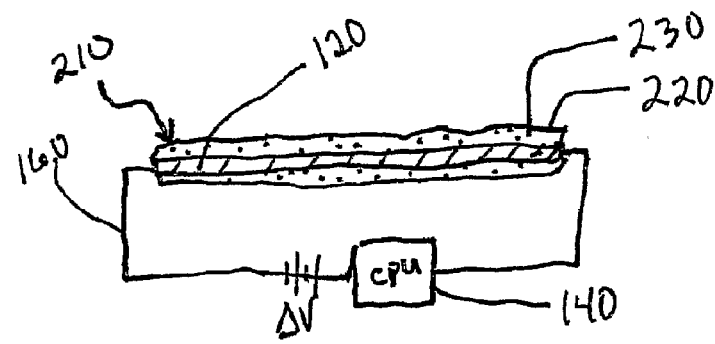
FIG 2A
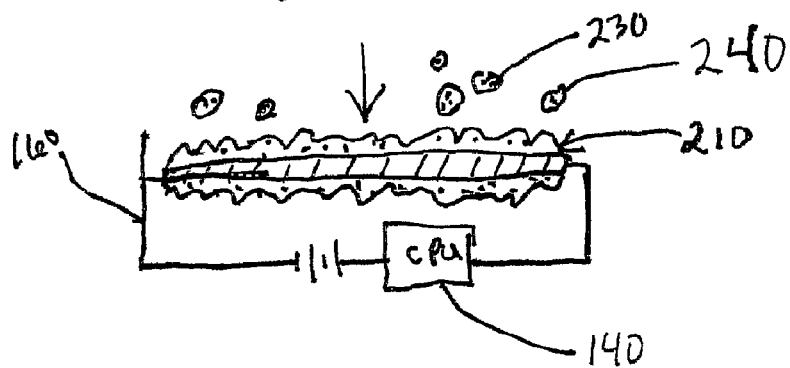
FIG 2B
Figure 2

COATED FILAMENT FOR EVAPORATION/CONDENSATION AEROSOL GENERATION OF THERAPEUTIC AGENTS AND METHODS FOR USING

RELATED APPLICATIONS

This application claims the benefit of U.S. Provisional Patent Application Ser. No. 60/622,256, filed Oct. 26, 2004; the disclosure of which is incorporated herein by reference in its entirety.

TECHNICAL FIELD

The presently disclosed subject matter relates generally to devices for generating aerosols of therapeutic agents and methods of using same. More particularly, the presently disclosed subject matter relates to aerosol generation devices and methods incorporating a heating element coated with a carrier substance and a therapeutic agent, wherein when the carrier is heated to its vaporization point by the heating element, the therapeutic agent is released as an aerosol from the heating element.

BACKGROUND

Aerosol delivery is important for a number of therapeutic compounds and for treatment of certain diseases. Various techniques for generating aerosols are disclosed in U.S. Pat. Nos. 4,811,731; 4,627,432; 5,743,251; and 5,823,178, each of which is incorporated herein in its entirety.

Local administration of aerosolized drug to treat diseases of the lung include asthma and chronic obstructive pulmonary disease (COPD), lung cancer, and anti-microbial therapy for infectious diseases of the airways. In addition, the lung is increasingly being considered as the portal of entry for a number of aerosolized drugs designed to act systemically. The benefits of administering macromolecular aerosols has been investigated for: insulin, growth hormone, various other peptides and proteins, and gene therapeutic agents.

Aerosol delivery to the airways offers advantages over other routes of administration for several disease states. Direct administration of drug to the lungs has pharmacokinetic and pharmacodynamic advantages, including: greater drug concentration at the intended site of action; reduced systemic side effects; rapid and extensive drug absorption due to the large surface area of the lungs; reduced enzymatic degradation due to the lower metabolic activity of the lung; and avoidance of the first-pass metabolism effect. In addition, drug absorption and dose is not significantly affected by ingested food, patients are familiar with administration techniques, and avoidance of the disadvantages associated with injections.

However, although aerosol delivery to human subjects has been performed routinely for over 50 years, and modified aerosol delivery systems have also been used with animal subjects, delivery systems are still surprisingly inefficient, can be difficult to use, achieve poor targeting, are irreproducible in delivery doses, and are generally inappropriate for newer applications such as gene therapy. Therefore, there remains a long-felt need for novel devices and methods that can produce effective aerosols of therapeutic agents for respiratory delivery to subjects.

SUMMARY

In one embodiment of the presently disclosed subject matter, an aerosol generation device is provided. The aerosol generation device can comprise a heatable filament and a composition coating the filament comprising a vaporizable carrier and a therapeutic agent, wherein when the filament is heated to at least the vaporization point of the carrier, the carrier vaporizes and releases the therapeutic agent from the composition to thereby form an aerosol comprising the therapeutic agent and the carrier. In some embodiments of the aerosol generation device, the heatable filament is comprised of a metal, a semi-conductive material, a thermo-electric polymer, a ceramic material, or a combination thereof. Further, in some embodiments, the heatable filament can be comprised of a metal selected from the group consisting of nickel chrome, tungsten, stainless steel, aluminum, and titanium. In some embodiments, the heatable filament can be a heatable coiled filament. Still further, in some embodiments, the heatable filament can comprise a plurality of heatable coiled filaments. In some embodiments, the plurality of heatable filaments can be arranged in parallel relation to one another and are affixed at an end to a substrate.

In another embodiment of the presently disclosed subject matter, an aerosol generation device is provided comprising a heating element having a surface and a composition coating at least a portion of the heating element surface and comprising a carrier and a therapeutic agent. When the heating element surface is heated to at least the vaporization point of the carrier, the carrier vaporizes and releases the therapeutic agent from the composition to thereby form an aerosol comprising the therapeutic agent and the carrier. In some embodiments, the carrier has a vaporization temperature that is less than the vaporization temperature of the therapeutic agent, and in some embodiments, less than the vaporization temperature of the therapeutic agent. In some embodiments, the carrier has a vaporization temperature that is less than 500° C., and in some embodiments is less than 300° C., and still further in some embodiments, less than 200° C. In some embodiments, the carrier is selected from the group consisting of capric acid, lauric acid, oleic acid, palmitic acid, stearic acid, phosphatidyl cholines (PC), polyethylene glycol (PEG), polyvinylpyrrolidone, lysine, leucine, polylysine, polyleucine, and combinations thereof.

In still other embodiments, the aerosol generation device can further comprise a power source for applying an electrical current to the heating element, such as for example a heatable coiled filament.

In some embodiments, the composition comprising the carrier and the therapeutic agent can further comprise a co-solvent, such as for example an alcohol, an aldehyde, a ketone, dimethyl sulfoxide, water, or combinations thereof. In some embodiments, the therapeutic agent forms a coating over at least a portion of an outer layer of the carrier and in alternative embodiments, the therapeutic agent and the carrier are intermixed in the composition. In some embodiments, the therapeutic agent comprises a small molecule, a polynucleotide, a polypeptide, or a recombinant virus. In particular embodiments, the therapeutic agent comprises a polynucleotide encoding a cystic fibrosis transmembrane conductance regulator polypeptide. In other particular embodiments, the therapeutic agent comprises a recombinant virus comprising a polynucleotide encoding a cystic fibrosis transmembrane conductance regulator polypeptide.

In some embodiments, the aerosol generation device is incorporated into a metered dose inhaler for use in pulmonary delivery of the therapeutic agent to a subject. In other embodiments, the aerosol generation device is incorporated into a rodent nose-only exposure chamber for use in pulmonary delivery of the therapeutic agent to a rodent subject. In some embodiments, the exposure chamber further comprises an elutriator positioned in flow communication between the aerosol generation device and the exposure chamber.

In still another embodiment of the present subject matter, a method of producing an aerosol is provided. In some embodiments, the method comprises: providing an aerosol generation device comprising a heating element having a surface and a composition coating at least a portion of the heating element surface, the composition comprising a carrier and a therapeutic agent; heating the surface of the heating element to vaporize the carrier and produce a heated vapor of the carrier and the therapeutic agent, thereby propelling the therapeutic agent from the surface of the heating element; and cooling the vapor to condense the carrier and the compound into an aerosol. In some embodiments, heating the surface of the heating element is by resistive heating of the heating element. Further, in some embodiments, heating the surface of the heating element is rapid. In some embodiments, cooling the vapor is by exposure of the vapor to ambient air.

In yet another embodiment of the presently disclosed subject matter, a method of administering a respiratory therapeutic agent to a subject is provided. In some embodiments, the method comprises administering an aerosol produced using an aerosol generation device as disclosed herein to the subject.

It is therefore an object of the present subject matter to provide an aerosol generation device and methods for evaporation/condensation aerosol generation of therapeutic agents and methods of using the same.

An object of the present subject matter having been stated hereinabove, and which is addressed in whole or in part by the present subject matter, other objects will become evident as the description proceeds when taken in connection with the accompanying drawings as best described hereinbelow.

BRIEF DESCRIPTION OF THE DRAWINGS

FIG. 2A is a cross-sectional view of a heating element coated with a carrier and a therapeutic agent.

FIG. 2B is a cross-sectional view of a heating element coated with a carrier and a therapeutic agent showing evaporation/condensation of the carrier and therapeutic agent and formation of an aerosol after heating of the heating element.

DETAILED DESCRIPTION

Figure 1:
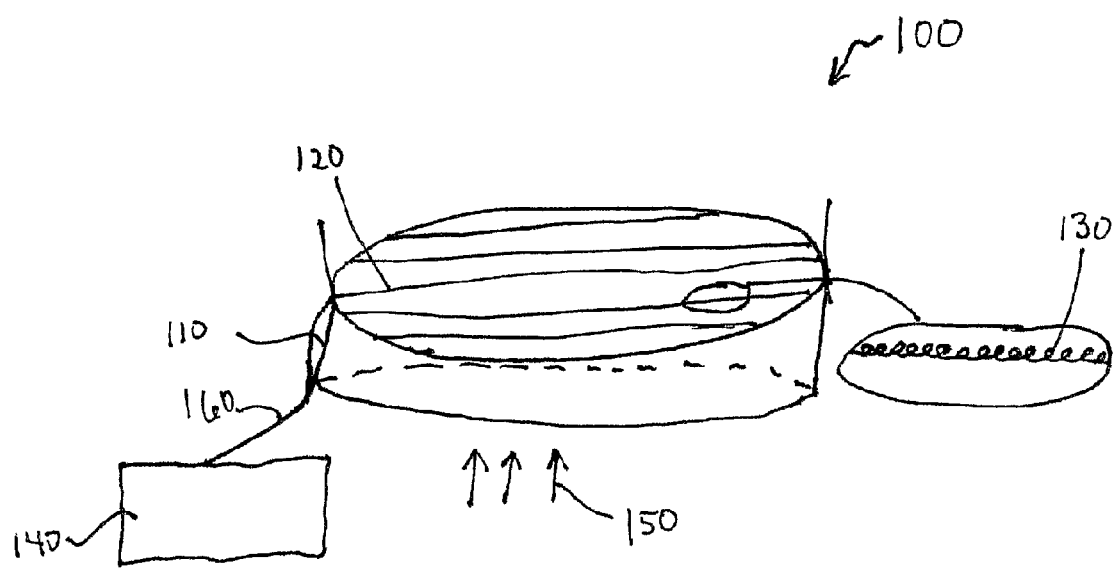
FIG. 1 is a schematic diagram of one embodiment of the aerosol generation device disclosed herein.

While inhaled pharmaceutical aerosols are a common and rapidly growing drug delivery platform, it is well established that these inhaler systems are inefficient and a low proportion of the dose reaches the intended site of delivery (e.g., the lungs). Thus, although it is appreciated that respiratory delivery of therapeutic agents in aerosol form to subjects can provide numerous advantages over other delivery platforms, at present, known aerosol generation and delivery devices are inadequate to provide the desired quality of aerosol generation and delivery. The aerosol generation device disclosed herein addresses the limitations of the current aerosol generation devices.

I. Aerosol Generation and Delivery

The lung has evolved to prevent the entry of unwanted airborne particles. Thus, physiological and anatomical features, such as airway geometry, humidity, mucociliary clearance and alveolar macrophages, combine to play a vital role in maintaining the sterility of the lung and are barriers to the therapeutic effectiveness of inhaled medications. In addition, a drug's efficacy may be affected by the location of deposition in the respiratory tract, the delivered dose, dosing regimen, and the disease state.

An aerosol is defined as a suspension of liquid or solid in the form of fine particles dispersed in a gas. For respiratory drug delivery, typical particles are between 1-10 µm. The ability of aerosolized drug to traverse the upper airways is a prerequisite for efficacy. Thus, engineering of aerosols for inhalation must account for the mechanisms of deposition and filtering of particles that occurs in the airways. Mechanisms of particle deposition in the respiratory tract include: inertial impaction, sedimentation (gravitational deposition), Brownian diffusion, interception, and electrostatic precipitation. All mechanisms occur simultaneously, but typically, inertial and sedimentation mechanisms are most important for aerosols with particles in 1-10 µm size range (of most importance in human lung deposition). The effectiveness of Brownian motion in depositing particles by diffusion is inversely proportional to particle diameters of those particles less than 0.5 µm and may be important in rodents. Thus, the most important factors controlling respiratory drug deposition are:

1. Characteristics of the aerosol: size, distribution, shape, electrical charge, density, and hygroscopicity;
2. Anatomy of the respiratory tract; and
3. Breathing Patterns: frequency, tidal volume, airflow.

Any approach to controlling airway deposition of therapeutic aerosols requires defined and/or engineered characteristics of the desired aerosol with respect to the anatomy and physiology of the target species.

I.A. Devices and Methods for Aerosol Generation and Delivery in General

There are a variety of known aerosol generation and delivery devices. Air jet nebulizers generate continuous aerosols in the 1-6 µm range and are used in ambulatory care for acute treatment of diseases. Pressurized metered dose inhalers and dry powder inhalers deliver 1-5 μm particles on the inspiratory flow of the patient. Evaporation/condensation aerosol generation devices have been used to create aerosols for a range of applications including pulmonary delivery. A variety of novel aerosol generation systems have also been developed recently. Of these devices designed for human aerosol administration, only nebulizers have also been used for delivery to the airways of mice, which can be useful as important experimental models of human disease. Even in humans, aerosols are delivered with low efficiency. On average, 10% of the dose placed in the nebulizer is actually deposited in the lungs. The dose actually delivered to experimental animals is often even lower.

Nebulizers were originally designed for local administration of anti-asthma medications to human lungs. They are relatively inefficient. Modulation of particle size, targeted deposition, chemical and physical stability of drug are problematic with nebulizers. Despite their widespread use in humans and animals, the aerosol characteristics are not ideal. Flow rates are much lower in mice airways and are not matched to the high flow rate generated from jet-nebulization of aqueous solutions (4-20 L/min). The output from 23 different nebulizer/compressor systems currently marketed has been analyzed. The mean airflow rate in these systems was 5.5 L/min and average mass median aerodynamic diameter (MMAD) was 6 μm.

In contrast to nebulizer aerosol output, the low tidal volumes in mice and other small animals indicate that slow moving and proximal aerosol generation may lead to higher lung deposition fractions. Other methods of administration of therapeutic agents to the airways of mice and other small laboratory animals have also been described. These methods are relatively invasive in that anesthesia, sedation, and/or intubation is required. Liquid instillation remains a commonly reported method despite erratic deposition patterns, toxicity concerns (associated with absorption from the lung periphery), and poor targeting. Spray instillation was used to obviate some of these issues associated with instillation. Liquids are spray-instilled into the airways of the animal using a nozzle placed proximal the carina (first bifurcation). A similar technique, dry powder insufflation, has shown some advantages to alternative methods due to increased stability. However difficulties in reproducible dosing appear common. The deposition of drug particles and efficiency of insufflation is dependent on powder and formulation characteristics, the force the operator applies to the syringe, and the exact location of insufflator nozzle in the airways.

Inhalation exposure chambers for rodents are commonly used in toxicological studies. In whole-body chambers an aerosol is introduced into a chamber containing animals, allowing whole body exposure, in addition to aerosol inhalation. Although anesthesia is not required and the approach is relatively simple, this method results in considerable drug deposition on the animals' bodies and subsequent ingestion during grooming. Thus, very small fractions of the total delivered dose are inhaled and effectively delivered to the lungs (site of action or absorption). Significant therapeutic agent is deposited on the chamber walls or on the animals skin. In nose only exposure chambers, designed to avoid problems associated with whole-body exposure, aerosol is introduced to a compartment to which only the nose of the animal is exposed. However, efficiency of delivery of aerosol to the lungs of mice remains low in typical set-ups reported in the literature. Radiolabeled aerosols were used to determine deposition patterns. Approximately 0.1 percent of the dose aerosolized was deposited in the mice and 0.0087 percent was deposited in the lungs. This efficiency is unsuitable for the delivery of expensive therapeutic agents (e.g. proteins, peptides, gene therapy agents). Reasons for poor efficiency relate to the airflow rates and volumes of inhalation compared with those of aerosol generation, the concentration of aerosol in the air and the droplet/particle size output.

I.B. Aerosol Generation and Administration Using Evaporation/Condensation Aerosols Condensation aerosol generation devices have been used to create aerosols for a range of applications including pulmonary delivery. Several types of generators have been discovered including the Rapaport and Weinstock generator; the Prodi generator; the Tu single stage generator; a laminar flow aerosol generator; and a capillary aerosol generator.

The principle of aerosol formation using evaporation/condensation aerosol generation devices is based on the production of a highly concentrated vapor which then undergoes cooling. The cooling of the saturated vapor results in supersaturation and subsequent condensation to form an aerosol of solid or liquid particles. Condensation methods are classified into three mechanisms: (1) cooling by expansion, (2) cooling by thermal conduction, and (3) cooling by rapid mixing with quenching gas. Thus, the basic approach to modifying aerosol characteristics is to control the concentration of vapor and nuclei (sites for initiating condensation, e.g., a therapeutic agent), and ensuring aerosol formation under stable conditions. Materials that are solid or liquid at room temperature and have boiling points of less than 500° C., preferably less than 300° C., and more preferably less than 200° C. can be suitable for this type of generator. Particle sizes resulting from evaporation/condensation generation devices can be estimated from the following relationship:

$$d_d = \left(\frac{6C_m}{\pi \rho_L N}\right)^{\frac{1}{3}}$$

where $C_m$ is the mass concentration of the vapor, $\rho_L$ is the density of the liquid, and N is the number concentration of nuclei. Thus, vapor concentration, formulation physicochemistry, and method of condensation (nucleation of vapor) are the main variables used for particle size modulation. Particle sizes from the nanometer to micron range have been reported for condensation aerosol generators.

Delivery of therapeutic agents using condensation aerosols can be achieved if the therapeutic agent and excipients (carriers) do not undergo thermal degradation or pyrolysis and if sufficient dose is delivered in the final aerosol. For gene therapy applications, the relative thermostability of adeno-associated virus (AAV) is well established. In fact this property underpins the conventional heat inactivation strategy used to remove contaminating adenovirus from rAAV stocks (56° C. for 1 hour). However, other gene therapy therapeutic agents as well as other therapeutic agents, including polypeptides and polynucleotides are inactivated by heat more readily. Thus, direct vaporization of the therapeutic agent into an aerosol is not a viable option for heat labile therapeutic agents.

As disclosed herein, a low vapor pressure carrier (e.g., a surfactant) to act as the primary evaporative component (or propellant) is proposed to allow aerosols to be produced at lower temperatures preventing vaporization of the heat labile therapeutic agent, while still allowing for formation of an aerosol comprising the agent. In addition, as provided herein, the duration of drug heating can be controlled (i.e., very brief rapid heating) such that thermal decomposition is minimal.

II. Evaporation/Condensation Aerosol Generation Device

Proposed herein is an evaporation-condensation aerosol generation device utilizing a heating element having a surface coated with a low vapor pressure carrier and a therapeutic agent. When the temperature of the heating element is raised, an aerosol suitable for inhalation therapy comprising the therapeutic agent is generated by evaporation/condensation of the carrier under low to moderate vaporization temperatures. By using a low vapor pressure carrier for the therapeutic agent, an aerosol can be formed at temperatures below those that would vaporize and/or inactivate a heat labile therapeutic agent. Further, parameters of the aerosol generation device are easily modified to control all aspects of the aerosol, including particle size and density and amount of therapeutic agent delivered.

Several other condensation aerosol generators have been described previously. For example, there are two condensation aerosol generators currently under development for aerosol delivery of therapeutic compounds to humans: ARIA™ Pulmonary drug delivery technology (Chrysalis Technologies Inc, Richmond, Va.) and STACCATO™ (Alexza Molecular Delivery Corporation, Palo Alto, Calif.). The ARIA™ technology is based on the aerosolization of a liquid flowing through a heated capillary tube using propylene glycol or water/ethanol as solvents. The STACCATO™ technology involves direct vaporization of a drug by rapidly heating a thin film of the drug to a temperature sufficient to convert a solid drug film into a vapor. These technologies provide evidence that therapeutic compounds can be delivered using condensation physics. However there are significant differences between the aerosol generation device of the presently disclosed subject matter and technologies currently available in the art.

The evaporation/condensation aerosol generation device disclosed herein has several novel features. Primarily, the therapeutic agent properties do not have to be selected for evaporation limits, thermal stability, or other thermal properties. The use of a carrier evaporation compound having a low vaporization point can be used so that condensation aerosols can be produced at much lower temperatures. The therapeutic agent can be coated onto the carrier, or dispersed within it (solution/solid dispersion) and then, when heated appropriately to a low temperature (vaporization temperature of the carrier), the carrier will carry the therapeutic agent as an aerosol. Thus, a wide variety of therapeutic agents, including heat labile agents, can be delivered as an aerosol with the use of a single aerosol generation device.

Further, the multitude of device, formulation and flow properties that can be altered within the presently disclosed aerosol generation device allows very tight modulation of aerosol characteristics, such as for example particle size, distribution, production rate, etc. In fact, aerosol production can be linked to airflow (patient inhalation for example) to tailor the aerosol to the exact conditions required. For example, filament properties including thickness, length, thermo-electrical properties (response times, conductivity, etc.), and coiling can be controllably altered to modify aerosol characteristics. Further, general device parameters including surface area of wire, electrical properties (wave form, power, etc.), airflow through wire, and numbers of wires utilized can be altered. Beyond modifications to the aerosol generation device, carrier properties can be modified such as for example physicochemical properties (vapor pressure, melting point, etc.) by selection of carrier or modification of chemistry of the carrier. Further, chemical excipients such as co-solvents can be incorporated to change aerosolizaton properties. Finally, properties of the therapeutic agent, such as concentration can be controlled.

Still further, in some embodiments of the presently disclosed device, the aerosol is generated on a heating element, which is a highly coiled wire, giving rise to a large surface area per unit volume of the wire. This facilitates large quantities of therapeutic agent and/or carrier to be coated to the wire if necessary. Thus, a wide dose range can be achieved with relative ease.

The aerosol generation device disclosed herein can also be incorporated into inhalers for delivery of therapeutic agents or into exposure chambers (whole body or nose only) for delivery to animals (particularly small animals) of therapeutic agents. The aerosol generation device disclosed herein can also be used for topical and transdermal administration of therapeutic agents, including for example small molecule drugs, polypeptides, and/or genes. The targeting of therapeutic agents to specific regions of lungs by the aerosol generation device is also a very attractive quality of the aerosol generation device.

FIG. 1 shows schematically one embodiment of the aerosol generation device disclosed herein. The system may take a variety of forms but essentially will contain those elements shown in FIG. 1, although each component can be modified as generally would be understood by one of skill in the art to achieve similar results without departing from the scope of the presently disclosed subject matter. As shown in FIG. 1, an aerosol generation device 100 comprises a body structure 110 housing at least one heating element 120. Heating element 120 can be a filament which conducts electrical current with a degree of resistance such that heating element 120 is heated to a desired temperature, preferably rapidly, by resistive heating. Heating element 120 can be a heatable coiled filament 130 in some embodiments. By coiling heating element 120, the surface area of an exterior surface of heating element 120 is increased, which permits greater substance loading capacity.

Heating element 120 can be a single filament, or it can be a plurality of filaments arranged to maximize aerosol generation, depending on the particular application. For example, as shown in FIG. 1, heating element 120 can comprise a plurality of filaments 130 arranged parallel to one another. The spacing between filaments 130 can be set according to the quantity of aerosol to be generated, with closer spacing of filaments resulting in greater aerosol generation up to a point, after which filaments 130 are too close to properly permit an air current, represented by arrows 150 in FIG. 1 to pass across filaments 130.

Other configurations, such as a meshwork of filaments 130 or filaments 130 on different planes with regard to one another are considered to fall within the scope of the presently disclosed subject matter as well. Further, heating elements 120 can be coiled filaments 130 as shown in FIG. 1, or even super-coiled filaments depending on the desired application.

Figure 9:
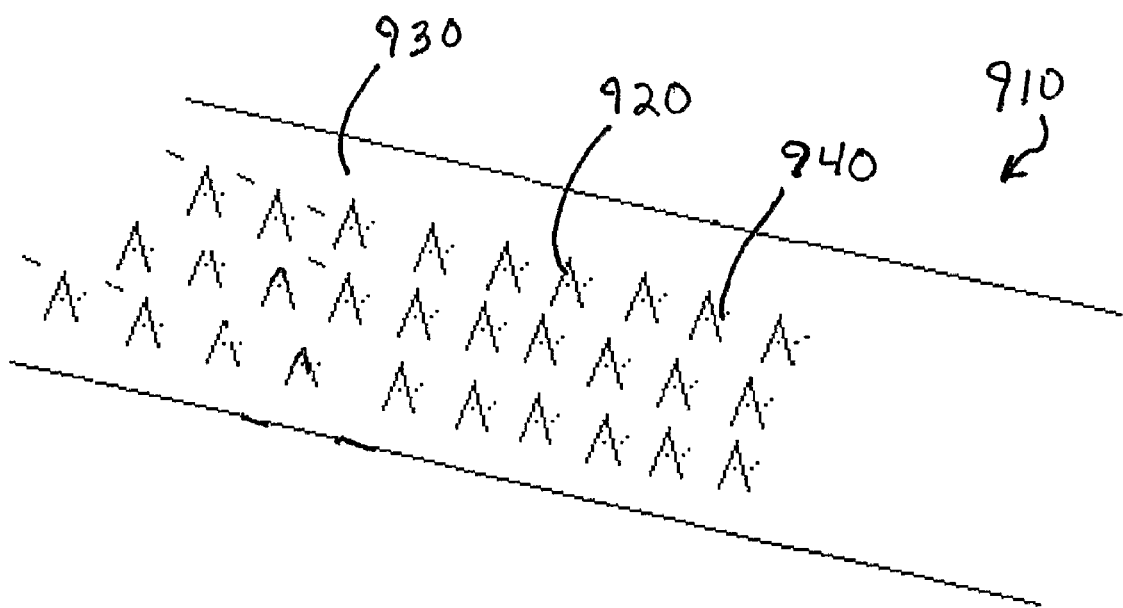
FIG. 9 is a schematic diagram of one embodiment of the aerosol generation device disclosed herein comprising a plurality of filaments.
Figure 4:
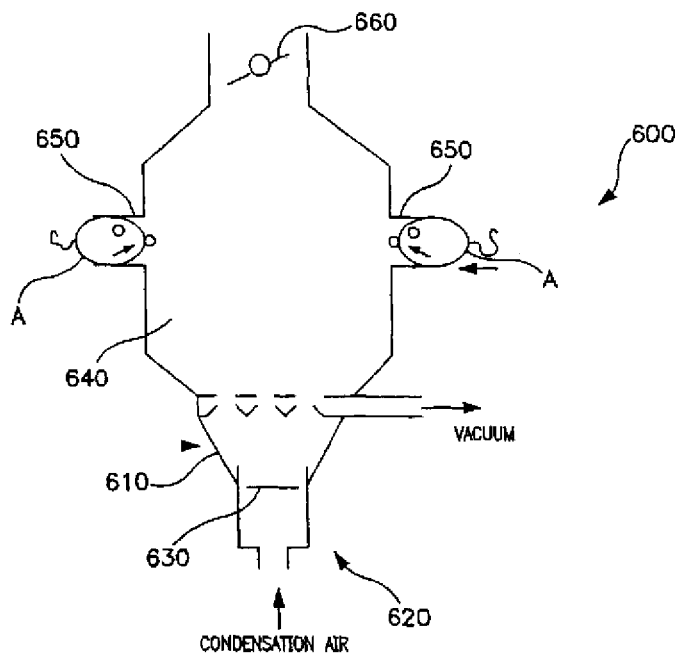
Figure 5:
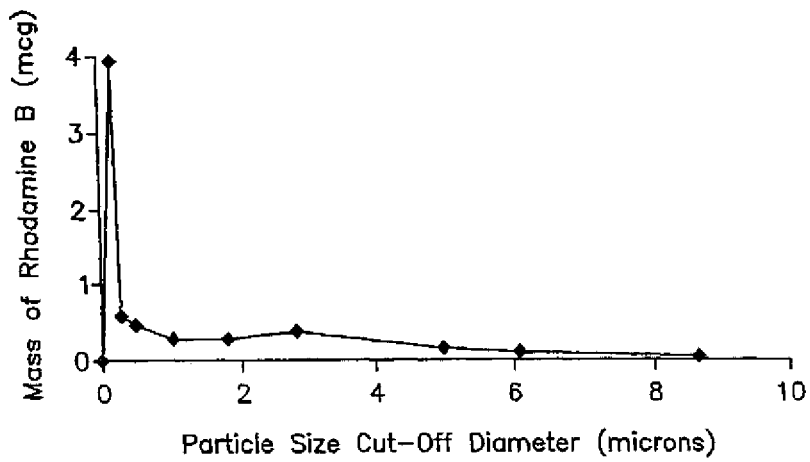

In one embodiment of the presently disclosed subject matter, as shown in FIG. 9, a heating element 910 comprises a plurality of filaments 920, preferably arranged parallel to each other along a long axis and affixed at one end to a substrate 930. Filaments 920 can be coated with a composition 940 comprising a carrier and a therapeutic agent by dipping filaments 920 into a heated liquid of composition 940. Upon standing, composition 940 will dry to a film and coat filaments 920, as shown in FIG. 9. If desired, filaments 920 along with part or all or the top surface of substrate 930 can be coated with composition 940 as well. When heating element 910 is heated to gene rate an aerosol from composition 940, only filaments 920 can be heated, or all or part of substrate 930 can be heated as well. Thus, if all or a portion of substrate 930 is coated with composition 940, it may be desirable to heat substrate 930 along with filaments 920 to increase aerosol generation capacity. Further, all of heating element 910 can be heated simultaneously, or only portions of substrate 930 and/or filaments 920 can be heated at a time, thus potentially providing multiple doses of aerosol on one heating element 910.

Filaments 920 can be arranged in very close proximity to one another to increase the surface area that can be coated by composition 940, further increasing aerosol generation capacity. Filaments 920 can have a tapered configuration as shown in FIG. 9, or have a variety of other configurations to maximize surface area as would be appreciated by one of skill in the art, such as for example a pin-like configuration, a crenete configuration, or a clavate configuration. Filaments 920 can be solid or have a hollow central cavity, which can be open at one or both ends. Filaments 920 can vary in diameter and length depending on the particular application, as would be appreciated by one of skill in the art. In some embodiments, filaments 920 can be produced having macro-scale dimensions. In other embodiments, it may be desirable to incorporate filaments 920 having micro-scale dimensions into heating element 910. On the micro-scale level, for example, hundreds or thousands of filaments 920, each being a few micrometers to a few hundred micrometers in length, can be affixed in close proximity to one another to substrate 930.

If resistive heating is used to raise the temperature of heating element 120, a current or power source 140, such as for example a battery or capacitor, can be linked to heating element 120 by, for example, connector wires 160 to direct electrical current from current source 140 through heating elements 120. Current source 140 can further include a variable power source and controller for permitting controlled variation of the electrical current passing to heating element 120, and therefore heat generation. Control over the current can be achieved by using a suitable programmable power supply (timer and current level) or using predictable discharge from a capacitor.

Heating element 120 of aerosol generation device 100 is coated with a composition 220, as shown schematically in FIG. 2A, which comprises at least a vaporizable carrier 220 and a therapeutic agent 230. As shown in FIG. 2B, when current source 140 passes an electrical current through heating element 120 via connector wires 160, heating element 120 is heated to a temperature where carrier 220 vaporizes and propels it and therapeutic agent 230 away from the surface of heating element 120. As carrier 220 cools, it condenses around nuclei (e.g., therapeutic agent 230) to form an aerosol 240 of appropriate size and concentration, as determined by apparatus properties, as disclosed hereinabove.

Heating element 120 can be a heatable coiled filament 130 (see FIG. 1) that conducts electrical current to heat filament 130 by resistive heating. In such embodiments, filament 130 is constructed from a material that conducts electrical current and exhibits particular resistance properties. For example, metals, semi-conductive materials, ceramic materials, or thermo-electric polymers can be incorporated into filament 130 to facilitate desired heating of filament 130. It is further within the scope of the presently disclosed subject matter to use composite materials comprising various metals, semiconductive materials, ceramic materials and/or thermo-electric polymers.

Exemplary metals for use as components of filament 130 include, but are not limited to nickel chrome alloys (nichrom), tungsten, stainless steel, aluminum, and titanium. Nichrom wire is particularly useful for incorporation into aerosol generation devices disclosed herein as it is a metal with a known relatively high resistively ($\rho=108$ µOhm/cm) for a conductor and sufficient thermal energy can be generated at low voltage levels for condensation aerosol production. Nichrom has good tensile strength to be coiled and manipulated and good thermal conductivity (13.4 W m$^{-1}$ K$^{-1}$ at 23° C.). Stainless steel is also suitable for use as it too can produce heat in required amounts for aerosol production using carriers disclosed herein. When selecting a material for use in manufacture of heating element 120, one of skill in the art will appreciate several properties of the material will be evaluated to determine whether the material is suitable, such as for example, thermal response times, maximal thermal response, and conductance dynamics (change in resistance with temperature, resistance stability, change in resistance over time). Thus, suitable thermo-electrical properties for heating element 120 include fast thermal response, predictable maximal temperature, and formable physical characteristics (for increasing surface area).

Vaporizable carrier 220 (see FIGS. 2A and 2B) is selected for incorporation into composition 210 based in part on its vaporization properties. It preferably will vaporize at a temperature at least below that of the vaporization temperature of therapeutic agent 230, and in some embodiments below the inactivation temperature of therapeutic agent 230. For example, in some embodiments, the vaporization temperature of carrier 220 is less than 500° C., in some embodiments less than 300° C., and in some embodiments less than 200° C. In some embodiments, carrier 220 is, for example, medium chain fatty acids, polymers, amino acids, polypeptides and/or phospholipids. Exemplary carriers useful as carriers include, but are not limited to, fatty acids such as capric acid, lauric acid, oleic acid, palmitic acid, and stearic acid; phospholipids, including phosphatidyl cholines (PC); polymers, including polyethylene glycols (PEG), and polyvinylpyrrolidone; and amino acids and polypeptides, including lysine, leucine, polylysine, and polyleucine. Further, in some embodiments, individual carrier components can be blended to provide further control over the evaporative process. For example, a carrier that is liquid at room temperature having a low vaporization temperature could be blended with one or more other carriers having higher vaporization temperatures to create a blended carrier having an intermediate vaporization temperature most appropriate for a particular application.

Properties of carriers suitable for use with the aerosol generation device disclosed herein can include: (1) appropriate evaporation/condensation dynamics; (2) general acceptance in the field for use in human and animal subjects (e.g., currently marketed, FDA approved, etc.); (3) compatibility with particular therapeutic agents, such as for example carriers beneficial in promoting gene transfer in the airways in applications wherein the therapeutic agent comprises polynucleotides; (4) no degradation during heating near or slightly above the boiling point of the carrier; and (5) assisting therapeutic agent entry into cells by, for example, transient membrane disruption, membrane fusion, or receptor mediated uptake (e.g., specific polypeptides).

In some embodiments, a co-solvent is further incorporated into composition 210. The co-solvent can provide solubility benefits to the carrier and/or therapeutic agent. Exemplary co-solvents for use in certain formulations include, but are not limited to, alcohols (e.g., ethanol), aldehydes, ketones, dimethyl sulfoxide, water, and combinations thereof.

Figure 3:
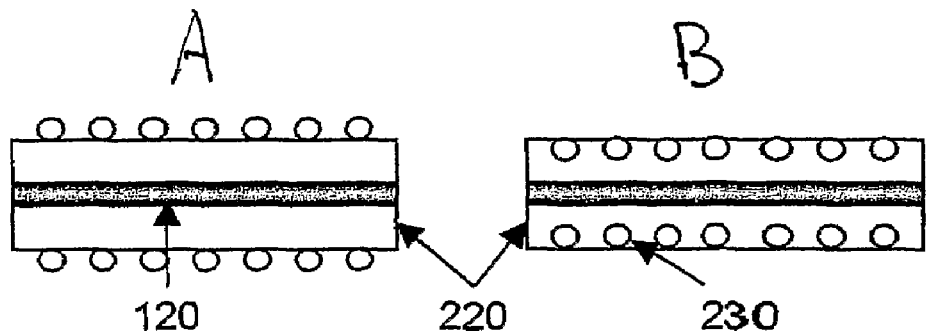
FIG. 3A is a cross-sectional view of a heating element coated first with a layer of carrier and then second with an additional layer of therapeutic agent.
FIG. 3B is a cross-sectional view of a heating element coated with a mixture of carrier and therapeutic agent.

Carrier 220 acts as a low temperature volatizing propellant to propel therapeutic agent 230 from the surface of heating element 120 prior to condensation into aerosol 240. See FIGS. 2A and 2B. Thus, how therapeutic agent 230 and carrier 220 are integrated into composition 210 will determine to some extent properties of propulsion of therapeutic agent 230 and the aerosol created by evaporation/condensation of carrier 220 and therapeutic agent 230. FIGS. 3A and 3B illustrate two exemplary embodiments of incorporation of carrier 220 and therapeutic agent 230 into composition 210.

Coating of therapeutic agent 230 on the surface of carrier 220 is shown in FIG. 3A, and can be preferable in some embodiments for thermal stability. In these embodiments, heating element 120 can be coated with carrier 220 via immersion into melted carrier 220. The thickness of coating can be determined by the surface tension of the liquid carrier system and the number of times heating element 120 is immersed. Increasing thickness can be achieved by repeated coating of heating element 120 until predetermined thickness levels are achieved, which can be identified by a number of techniques known in the art, including for example using microscopy. Following heating element 120 coating, therapeutic agent 230 can be loaded onto the surface of carrier 220. This can be achieved by either immersion of coated heating element 120 into a solution of therapeutic agent 230, or adhesion of a freeze-dried powder of therapeutic agent 230 to the coated heating element 120 surface, for example.

Integration of therapeutic agent 230 with carrier 220 in corn position 210 is shown in FIG. 3B and can be preferable in some embodiments, for example, for increasing dose delivered and efficient aerosolization of therapeutic agent 230. Integration of therapeutic agent 230 into carrier 220 can be achieved via emulsification of carrier 220 with an aqueous solution of therapeutic agent 230. Following the formation of an emulsion, heating element 120 can be coated with the formulation and allowed to dry, whereby coating undergoes solidification. Integration can be similarly achieved if a suitable co-solvent is used to solubilize therapeutic agent 230 (from, for example, a freeze-dried cake) and carrier 220.

Since carrier 220 is selected in part based on its low vapor point, a broad range of therapeutic agents 230 can be incorporated into composition 210 for production of aerosols. In particular, therapeutic agents 230 that would be otherwise lose activity if incorporated into a prior art aerosol generation device are well-suited for use in the aerosol generation device of the presently disclosed subject matter. Exemplary therapeutic agents that can be incorporated into the presently disclosed aerosol generation device include but are not limited to small molecule drug compounds, polynucleotides (e.g., encoding therapeutic peptides), polypeptides, and recombinant viruses encoding or carrying therapeutic peptides. In some particular embodiments, the therapeutic agent is a polynucleotide encoding a cystic fibrosis transmembrane conductance regulator (CFTR) polypeptide, either alone or incorporated into a delivery vehicle, such as for example a liposome or a recombinant virus. The CFTR polypeptide is defective in patients suffering from cystic fibrosis (CF) and therefore providing an active CFTR polypeptide to CF patients, e.g., via gene therapy, has been proposed as an effective therapy for CF. These therapeutic agents will not be deactivated by high temperatures when used in the presently disclosed aerosol generation device as the carrier selected has a low vapor point.

In some embodiments, therapeutic agent 230 can comprise a recombinant virus or other vector for delivering a polynucleotide or polypeptide to a cell within an aerosol generated by the presently disclosed aerosol generation device. Naturally occurring viruses are attractive vectors for gene therapy due to their evolved ability to introduce their own viral nucleic acid (RNA or DNA) into the host cell nucleus, leading to the expression of viral genes that promote viral replication. A summary of exemplary vectors for airway gene transfer are presented in Table 1.

TABLE 1

Vectors for Airway Gene Transfer*

| Vector | Maximum cDNA insert size (kbp) | Duration of expression | Immune/ inflammatory response | Risk of insertional mutagenesis |
|---|---|---|---|---|
| Adenovirus | 7->30 | Transient | Humoral/cell | Minimal |
| Adeno-associated virus | 4.5 | Long term | Humoral | Low |
| Retrovirus | >7 | Long term | None | Yes |
| Polymers | >10 | Transient | Unknown | Minimal |
| Cationic liposomes | >10 | Transient | Inflammatory | Minimal |

*Adapted from Johnson (2003) In: Templeton & Lasic (eds) Gene Therapy: Therapeutic Mechanisms and Strategies. Marcel Dekker Inc., New York; incorporated herein by reference.

In some embodiments, therapeutic agent 230 is an adeno-associated virus (AAV) comprising a polynucleotide encoding a therapeutic polypeptide, which can then be delivered to the lungs of a subject in need of treatment via inhalation of an aerosol generated with the presently disclosed aerosol generation device. The principle behind using a carrier is to reduce the thermal stress on the therapeutic agent through a reduction in the heat required for vaporization to occur. Although AAV vectors are generally considered to be more resistant to thermal and chemical degradation than many viral vectors, even AAV vectors may not be chemically or thermally stable in a particular carrier. Incompatibility of the AAV, or another virus or vector, with formulation carriers can be obviated using several strategies. The AAV vector can be coated onto the carrier, rather than making a solid dispersion (solution) as described hereinabove, for example. This reduces the proximity of the vector to the heat source (heating element surface). Another strategy that can be employed is to minimize the residence time of the vector on the heating element, which will decrease the propensity for thermal degradation. This can be achieved by increasing heating rates so that the vaporization temperature of the carrier is reached rapidly. In some embodiments, the rate of rapid heating is about at least 5° C./second or more. However, the heating rate is greatly dependent on the vaporization point of the carrier, with it being desirable to have a more rapid heating rate for a carrier with a higher vaporization rate. Alternatively, or in combination, different carriers can be selected. Thus, in embodiments wherein therapeutic agent 230 comprises a recombinant virus, the virus vector can deliver effectively a polynucleotide encoding a therapeutic polypeptide directly into a target cell in a subject, wherein the cell can produce the encoded polypeptide in therapeutic quantities.

In some embodiments of the presently disclosed subject matter, the aerosol generation device disclosed herein can be incorporated into a delivery device, such as for example a metered dose inhaler (MDI) or an exposure chamber for delivery of the generated aerosol to the lungs of the subject.

A common type of MDI used is the pressurized metered dose inhaler (pMDI). This type of inhaler typically uses an ozone-depleting CFC propellant such as Freon, but recent pMDI systems have used alternatives such as hydrofluoroalkane (HFA) propellant in lieu of CFC propellant. Pressurized metered dose inhaler (pMDI) devices typically incorporate a propellant, under pressure, to generate a metered dose of an aerosol through an atomization nozzle. Upon actuation of an actuator by a subject, a metered volume (typically between 20-100 µl) of a drug/excipient/propellant blend is expelled from a canister through a metering valve. The metered volume passes through an atomization orifice where primary atomization occurs and whereby the metered volume is transformed into an aerosol spray plume consisting of individual atomized droplets. A typical pMDI can further comprise a spacer chamber for increasing the distance between atomization orifice and the throat of a subject, thereby improving peripheral lung deposition.

The aerosol generation device disclosed herein can be incorporated into an MDI-like device in lieu of the atomization elements of the MDI and without the need necessarily of propellants. Instead, upon actuation of the heating element by the subject, an aerosol is produced comprising the active agent, as disclosed herein, and transmitted into the airway of the subject. The heating element can be actuated using a pushbutton mechanism, for example, or even by detection of a negative pressure created by the subject drawing in a breath through the mouthpiece of the device.

In some embodiments of the presently disclosed subject matter, the aerosol generation device disclosed herein can be incorporated into an exposure chamber for delivery of the generated aerosol to the subject. Exposure chambers are particularly useful for delivering aerosols to animals, including small laboratory animals such as rodents. The animal can be completely contained within the exposure chamber or only a portion of the animal can be placed in the exposure chamber, such as for example the nose of the animal.

As is well known to those skilled in the art, mouse models of human disease are an important element in biomedical research. The development of an efficient aerosol delivery system would significantly increase the utility of these models for evaluating lung disease and inhaled therapy. Current methods of drug administration to mice use liquid instillation or nebulization. These methods have serious practical disadvantages of very low efficiency (i.e., inability to deliver small <3 µm particles due to large volume low concentration aerosols inhaled at small inspiratory flow rates) culminating in poor targeting. In addition, animals may need anesthesia or surgical procedures. With the current and expected development of mouse models for various disease states (e.g., asthma, pulmonary hypertension, SARS, cystic fibrosis, etc.), there exists an urgent need for a murine aerosol drug delivery system. However, the design of a delivery system must account for the specific physicochemical and aerodynamic properties of the aerosol required to deliver and target particle deposition through the anatomical and physiological barriers of the murine airways.

Despite the need for effective delivery systems there appears to have been few advances on the currently inadequate approaches. Recent reports have demonstrated that current methods are extremely inefficient. In contrast to humans, laboratory animals such as rats, mice, hamsters, and guinea pigs are all obligate nose breathers. In addition, there are significant anatomical and physiological differences between the lungs of animals and the human respiratory system. Although the optimum particle size for alveolar deposition is approximately the same for humans and mice (3 µm), tracheobronchial deposition differs between humans (6 µm) and mice (~4 µm). In addition, several key respiratory parameters are at least an order of magnitude different for humans compared to mice. Thus, efficient delivery of drug to the lungs, with a defined aerosol, is difficult using current technology. In fact, a recent study, employing commonly described experimental apparatus, determined that approximately 0.1% of the dose was delivered to the mouse, and less than 0.01% was delivered to the lungs of the mouse. Poor efficiency can be attributed to the use of devices designed for humans in animals that are physiologically different: obligate nose breathers, small tidal volumes, and different particle size dependent aerosol deposition characteristics (due to anatomical differences). Despite the low efficiency of delivery to mice and other small laboratory animals, the importance of these human surrogates in health research for efficacy and safety is expected to increase. It is clear that active therapeutic agents may be dismissed as ineffective simply because they have not been delivered efficiently or to the site of action as aerosols.

Figure 4:
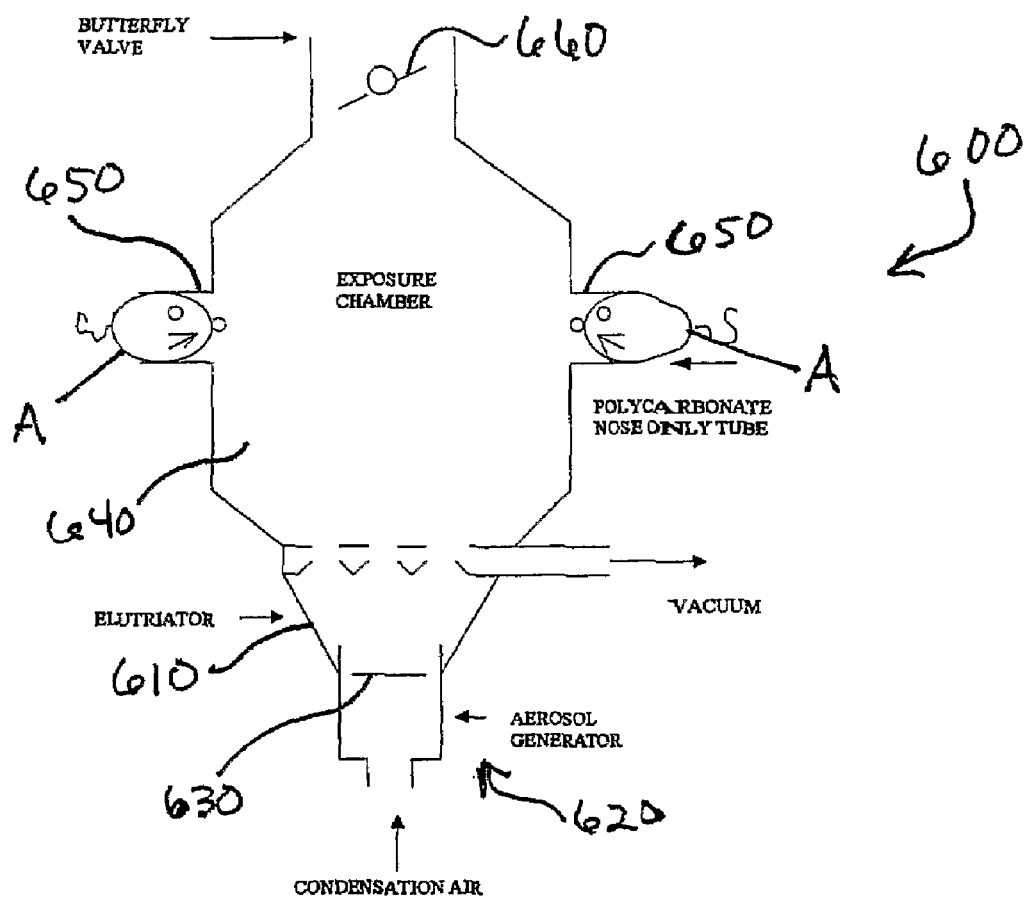
FIG. 4 is a schematic diagram of a mouse nose-only exposure chamber with features to allow aerosol concentration and controlled flow rates. (Two exposure positions are shown, but multiple exposure conditions can be present).

The presently disclosed subject matter provides for an aerosol generation device incorporated into an exposure chamber for use in delivering aerosols generated as disclosed herein to animals, such as rodents. An exemplary combined aerosol generation device and exposure chamber device 600 is shown in FIG. 4. In some embodiments, the exposure system will incorporate design features from typical nose-only exposure chambers. However, further improvement can clearly be achieved for mice aerosol delivery. Mice are obligate nose breathers with an approximate respiratory rate of 94-163 cycles/min and a tidal volume of between 0.09-0.23 ml. Thus, a volume of approximately 8.5 ml to 35 ml is breathed per minute. Aerosol presentation to the exposure chamber will account for this to avoid excessive loss of dose. An elutriator 610 can be employed in some embodiments to concentrate aerosol into 10% of the initial volume of air. By introducing aerosol into a reservoir with a modest positive pressure a standing cloud can be generated from which the animals can passively inhale the aerosol.

With reference to FIG. 4, exposure chamber 600 comprises an aerosol generator 620 having a heating element 630 as described herein above. Heating element 630 is positioned in flow communication with an exposure chamber 640. Elutriator 610 can be interposed between aerosol generator 620 and exposure chamber 640. Animal subjects A are exposed to the generated aerosol present in exposure chamber 640 via nose-only receiving tubes 650. Exposure chamber 640 can be evacuated through actuation of a butterfly valve 660.

Excessive vapor may not condense to aerosol prior to delivery to exposure chamber 640. Inhalation of vapor is undesirable due to potential toxic effects. Thus, exposure chamber 640 includes, previously referenced elutriator 610, which can be utilized if significant vapor is detected in the aerosol (e.g., via laser diffraction and GC). Elutriator 610 also functions to increase the aerosol concentration. In addition, in some embodiments, use of a temperature controlled condensation trap can be employed.

III. Methods of Using Aerosol Generation Device

The presently disclosed subject matter further provides methods of using the aerosol generation devices disclosed herein. In one embodiment, the presently disclosed subject matter provides a method of producing an aerosol. The method can comprise first providing an aerosol generation device as disclosed herein comprising a heating element having a surface and a composition coating at least a portion of the heating element surface, the composition comprising a carrier and a therapeutic agent. The method can next comprise heating the surface of the heating element to vaporize the carrier and produce a heated vapor of the carrier and the therapeutic agent, thereby propelling the therapeutic agent from the surface of the heating element, and finally, cooling the vapor to condense the carrier and the compound into an aerosol. In some embodiments, the surface of the heating element is heated using resistive heating as described herein above and in some embodiments the heating is rapid to prevent thermal degradation of the active agent. Further, in some embodiments, the vapor is cooled to reduce the aerosol by exposure to ambient air.

In an experimental embodiment, an aerosol generation device as disclosed herein was utilized to produce aerosols. The device was manufactured with the following parameters: a heating element of nichrom wire (20 cm length, 0.405 mm diameter) coiled 16 times; a constant voltage of 2 V; ambient airflow conditions; a carrier comprising capric acid (99.9% w/w); and RHODAMINE B (0.01% w/w) incorporated into the carrier as a marker since it is readily detectable using fluorimetry at ng/mL concentrations and as representative of a therapeutic agent. The 20 cm length of wire, coiled to an internal diameter of 0.723 mm, was loaded with 35 mg of capric acid/RHODAMINE solution (solid dispersion).

Figure 5:
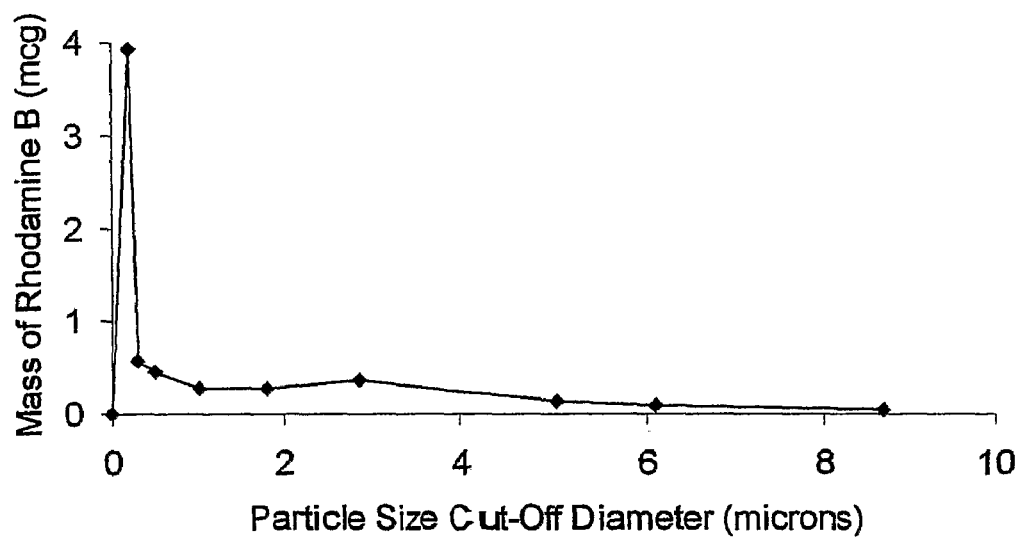
FIG. 5 is a graph showing particle size distribution of condensation aerosols generated from an aerosol generation device disclosed herein.

Preliminary particle size analysis was performed using inertial impaction methods as generally known in the art (ANDERSEN 8-stage non-viable inertial impactor; Smyrna, Ga., U.S.A.). An example of the particle size distribution obtained using a capric acid/RHODAMINE formulation is shown in FIG. 5. Mass median aerodynamic diameters (MMAD) were calculated to be around 0.23 µm. Particle size analysis can also be performed or confirmed using laser diffraction to determine the volume diameters of the aerosol particles, as is generally known in the art. In addition, microscopy methods can be employed to visualize particle size and morphology (e.g., scanning electron microscopy (SEM)). Additionally, time-of-flight aerosol particle size analysis can be performed (lower particle size limit ~1 µm) (AEROSIZER, TSI, Hadley, Mass.). A quartz crystal microbalance cascade impactor (Model PC-2AS/SK76, California Measurements, Sierra Madre, Calif., U.S.A.) can be used as a complementary sizing method.

Heating rates were calculated for the nichrome wire at different potential differences using a conductive temperature probe. Heating profiles were approximately linear over the time scales studied. At 2 volts, temperatures increased at 1.05° C./second, at 4 volts temperatures increased at 2.87° C./second, and 6 volts the increase was at 5.86° C./second. These heating rates were deemed suitable (relatively low voltages required for a wide range of heating rates).

Figure 6:
FIG. 6 is an image of an aerosol generated from a heating element coated with a low vapor point carrier.
Figure 7:
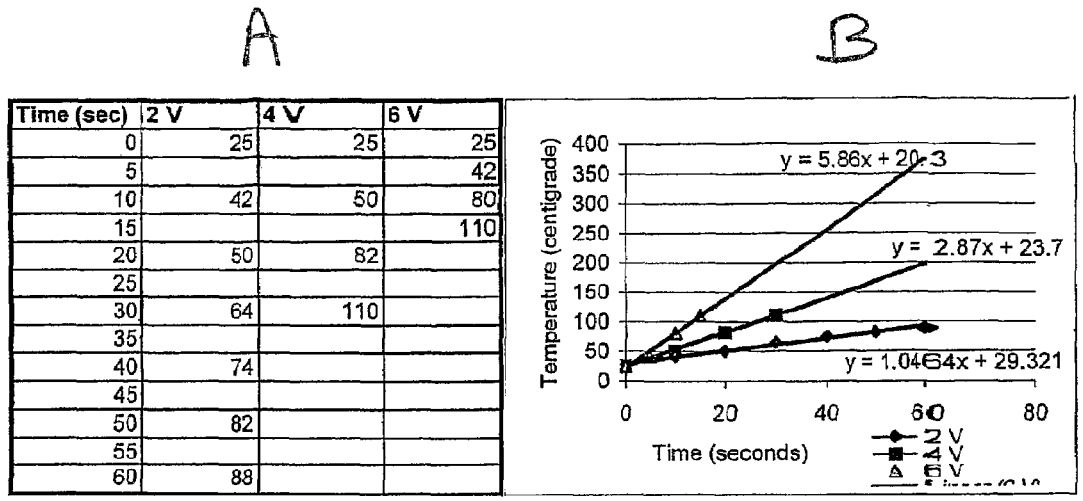
FIGS. 7A and 7B are respectively, a table and graph of data from the table showing heat production and rates of heating of a heating element at different voltages.
Figure 8:
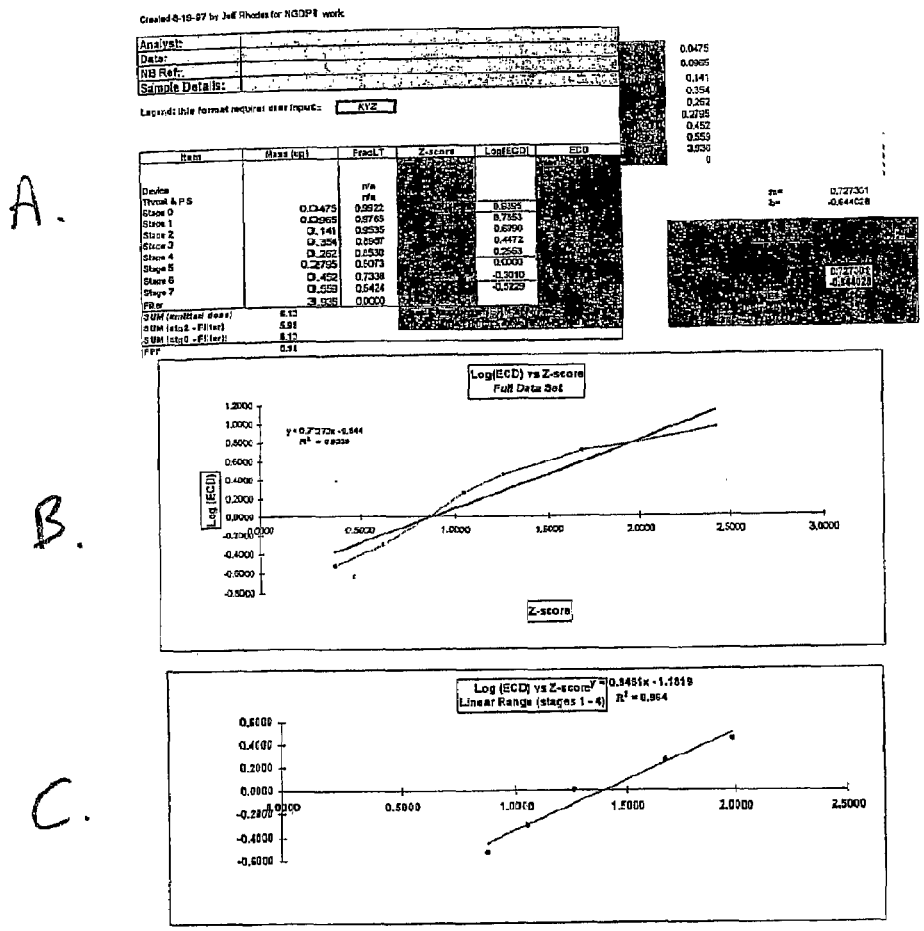
FIGS. 8A-8C are a table and graphs of data from the table, respectively, showing results of an aerosol particle sizing experiment.

The aerosol generation device satisfactorily produced measurable volumes of aerosol containing the RHODAMINE marker. Images of aerosol generation are shown in FIG. 6 utilizing the aerosol generation device.

In some embodiments, the presently disclosed subject matter provides a method of administering a therapeutic agent to a subject. The method comprises administering an aerosol produced with an aerosol generation device as disclosed herein and comprising the therapeutic agent to the subject. The subject inhales the aerosol using, for example, a delivery device such as an MDI. The aerosol generation device and the delivery device can be incorporated into a single apparatus, as disclosed hereinabove.

It may be desirable to target delivery of the aerosol comprising the therapeutic agent to specific regions of the lung to maximize the therapeutic effect and minimize unwanted side effects. The location of receptors and disease foci varies within the respiratory tract and therefore successful therapy may depend on targeting these sites. For systemic administration, targeting the periphery may be advantageous as the rate of absorption is twice as fast as that from the central airways. Cost-effectiveness of therapeutic agent delivery can also be improved due to greater efficiency of delivery (e.g., expensive gene therapy agents). DNA transfer to airway epithelial cells for treating particular disorders, such as for example CF, may require targeted delivery to the region of the lung where the defect is manifested (e.g., in CF gene therapy, the CFTR polypeptide can be targeted to epithelial cells involved in chloride ion transport, such as bronchial airways or respiratory zone). In addition, targeted delivery of aerosolized antibiotics to regions of recurrent infections in disorders involving the lungs, such as respiratory infections secondary to CF, is highly desirable.

Simple serial targeting of aerosol is defined as drug deposition differences between the conducting airways and the alveolar regions. Diseased lungs provide unique challenges for targeting due to inter-individual variability in disease progression and location. However, simple serial targeting of aerosols is likely to be beneficial if the correct location of therapeutic action has been identified.

Regional targeting of lung via modulation of aerosol particle size and flow characteristics can be achieved using the aerosol generation devices disclosed herein. Regional aerosol deposition and transfection rates can be evaluated using simple serial definitions of lung regions (central versus peripheral airways), for example.

In some specific embodiments, aerosols are generated comprising a polynucleotide encoding the CFTR polypeptide as the therapeutic agent. In some embodiments, a recombinant viral vector in the aerosol carries the CFTR polynucleotide. The aerosol can be generated to maximize delivery to a particular subject. In some embodiments, the aerosol is generated specifically for administration to a human subject suffering from CF and in other embodiments, the aerosol is generated specifically for administration to an experimental animal model subject, such as a rodent, manipulated to model human CF disease, e.g., a transgenic CF mouse.

Mutations in the CFTR gene give rise to CF. This inherited disorder is common and occurs in approximately one of every 3,200 live Caucasian births. The autosomal inheritance of this monogenic disorder in which heterozygotes are phenotypically normal has lead to the designation of CF as the prototypical disease for investigation of gene therapy to the lung. The abnormality of the CFTR protein leads to a number of pathological and biochemical disease states including chronic lung inflammation and infection, pancreatic obstruction. Patients with CF suffer from progressive lung destruction and respiratory failure. According to the CF Foundation's National Patient Registry, the median age of survival for a person with CF is 33.4 years.

Investigations have been conducted to evaluate clinical safety and efficacy of gene transfer vectors delivered by airway administration to CF patients. There are numerous clinical gene transfer safety and efficacy trials currently underway (see the National Institutes of Health Genetic Modification Clinical Research Information System (GeMCRIS) website). Preliminary results from an adeno-associated virus clinical study have been reported. In this Phase II CF clinical trial, tgAAVCF displayed a strong safety profile and was associated with positive trends in lung function and levels of inflammatory cytokines, both considered important measurements of disease. However, in this and other studies, only modest evidence of gene transfer was observed and, generally, the efficiency and efficacy of gene transfer failed to met expectations as therapy did not correct functional defects previously observed.

Low efficiency of gene transfer can be ascribed to a combination several barriers including contents within the airway lumen (mucus, inflammatory milieu, glycoconjugates), vector specific barriers affecting binding and entry (receptor localization and endocytic capacity, nuclear translocation), factors limiting transgene expression post-nuclear entry, and drug delivery efficiency.

This lack of success has promoted the exploration of mechanisms and barriers to gene transfer. Significantly, the investigation of gene transfer has been aided by the concurrent development of a number of murine models for CF. Aerosols comprising polynucleotides encoding CFTR, either alone or in a virus vector, can be generated by the aerosol generation devices disclosed herein and therefore hold great promise for treatment of subjects suffering from CF. Further, these aerosols can provide a vehicle for delivering experimental therapeutics, including gene therapy therapeutics, to CF animal models for efficacy testing.

EXAMPLES

Example 1

Aerosol Generation

Studies were conducted to determine the aerosol generation potential from a fatty acid-hot filament aerosol generation device.

Materials and Methods: "Resistance wire" or "thermal wire" was selected from several different materials due to availability. Nichrom (nickel/chrome) wire was used for the present Example. This type of wire is used for many different applications, including for resistance heating applications (e.g., thermal foam cutters).

Approximately 15 cm lengths of a 36 gauge wire were prepared. The wire was wound around a nail to create tight coiling so that the fatty acid could be coated with high loading capacity.

The fatty acids utilized in the present example were oleic acid, lauric acid and capric acid. Oleic acid is liquid at room temperature and requires coiling to add surface tension for significant coating to occur.

The lauric and capric acids were heated to just above melting temperature until the fatty acid was completely liquid, the coiled wire was then immersed in a beaker containing the liquid fatty acid. The beaker was left to cool, and the fatty acid solidify. Once the fatty acid had solidified, the wire was removed. However, it is not necessary to wait until after solidification of the fatty acid, but only until viscosity is sufficiently high to adsorb the fatty acid to the wire. The wire was then attached to an electrical supply (D.C. variable power supply 0-12V, OLYMPUS, Melville, N.Y., U.S.A.), which was utilized as a current source to supply electrical current to the wire for resistive heating of the wire. Various voltages were tested for appropriate heating.

Results: Aerosols were generated into still air or into a flowing air stream (e.g., a fume hood). Voltages required to aerosolize the fatty acid carrier were low to moderate (2-12V). An image of an aerosol generated is shown in FIG. 6.

Conclusion: These and similar materials appear suitable for inclusion into an aerosol generation device as disclosed herein.

Example 2

Aerosolization of Model Drugs Using Aerosol Generation Device

Studies were conducted to determine the capacity of the aerosol generation device to generate evaporation-condensation aerosols of a model drug compound. The aerosol generation device used incorporated capric acid as a carrier coating over nichrom wire and Rhodamine B as the model drug compound.

Materials and Methods: RHODAMINE B was added to a first beaker containing capric acid and a second beaker containing capric acid with ethanol as a co-solvent. RHODAMINE and capric acid with or without ethanol were heated gently on a hotplate/stirrer. Mixtures were coated to a wire filament as used in Example 1.

Results: RHODAMINE-capric acid mixtures were not easily miscible without a co-solvent. Crystalline RHODAMINE often did not dissolve rapidly or completely. Adding a co-solvent (ethanol) resulted in a molecular dispersion of the RHODAMINE in the fatty acid. Upon cooling, the fatty acid solidified and was suitable for coating onto the wire. Upon heating the wire, aerosols were generated that contained the RHODAMINE marker.

Conclusion: Therapeutic agents (e.g., drugs) can be included in the fatty acid carrier and upon vaporization of the carrier and condensation of the carrier and therapeutic agent and aerosol comprising the therapeutic agent can be generated. Depending on the nature of the carrier and therapeutic agent a co-solvent, such as ethanol, can be used to improve miscibility.

Example 3

Characterization of Generated Aerosols

Studies were conducted to determine physical properties of aerosols generated using the aerosol generation device. Examined characteristics of the wire filament used included resistance, heat production, and electrical properties. Characteristics of aerosol generation using the model carrier system and a fluorescent probe (as model of a therapeutic agent) included mass deliverable, aerosol production rate, and particle size estimates.

Materials and Methods:

Wire Resistance Measurements:

Wire was measured to 20 cm and cut from source coil; and a multimeter was connected to each end of wire and resistance measured.

Heat Production Measurements:

Thermal generation from the 20 cm length of wire was measured using a THERMOLYNE digital pyrometer probe (Dubuque, Iowa U.S.A.);

Surface measurement where probe tip temperature is measured. Tip is 3 mm in diameter, cylindrical and made of stainless steel;

2V was applied across wire for 2 minutes and temperature change was measured over time;

Wire was coiled around probe (16 coils of 3.0 mm diameter to form coiled length of around 5 cm).

A second method of heat production measurement using a mercury bulb thermometer was used as well because of conductance short-circuiting of the nichrome wire by the stainless steel probe:
  0.6 cm (6 mm) mercury bulb;
  9 coils;
  temperature ±1° C. was recorded for 60 seconds or until temperatures reached 110° C.;
  2, 4, and 6 volts were tested.

Mass Deliverable/Production Rate Procedure:

A model formulation of capric acid, Rhodamine B and ethanol was prepared as follows:
  4 g of capric acid was weighed;
  0.01 g of RHODAMINE B was weighed; and
  2.275 g of ethanol added.

In a beaker these components were mixed and heated gently until all the RHODAMINE and capric acid had melted. The beaker was then lightly chilled (with crushed ice) and final weight of beaker measured. 0.1 g of ethanol was driven off during heating. The solid formulation was found suitable for coating a coiled wire filament.

Particle Size Estimation Procedure:

Particle size was estimated by generating an aerosol from the wire, using capric acid and RHODAMINE B as formulation coated onto the 20 cm coiled wire. The aerosol was generated at constant 2V until the loaded formulation was depleted. Approximately 0.04 g for formulation was loaded on to the wire. The aerosol was drawn into an Andersen 8-stage non-viable impactor (GRASEBY ANDERSEN, Smyrna, Ga., U.S.A.) at 28.3 Lpm airflow. The mass of Rhodamine deposited on each stage was determined using UV/VIS spectroscopy.

Results:

20 cm of wire had approximately 2 ohms (Ω) wire resistance as measured by the multimeter.

Figures 6, 7A:
Figures 7B, 8A:
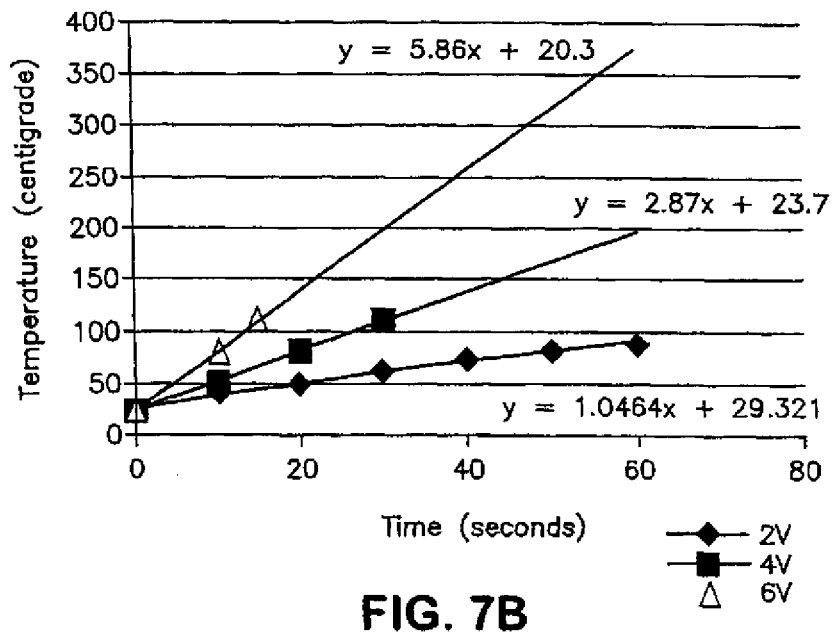

Heat production and rates at different voltage levels are shown in FIGS. 7A and 7B.

Mass deliverable was determined as follows:
  Single coating of formulation one wire=22 mg;
  Double coating of formulation yielded weigh=41 mg.

Thus, it was determined substantially all mass loaded can be delivered into an aerosol utilizing the aerosol generation device.

Figure 8B:
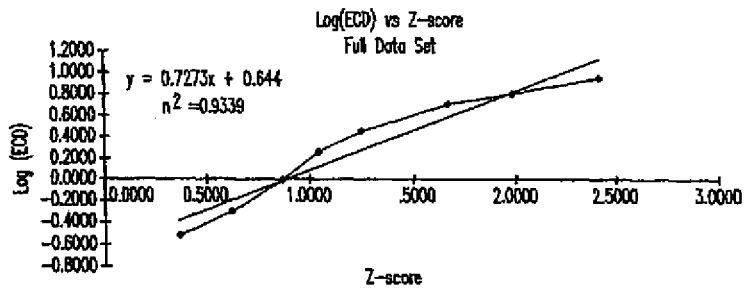
Figure 8C:
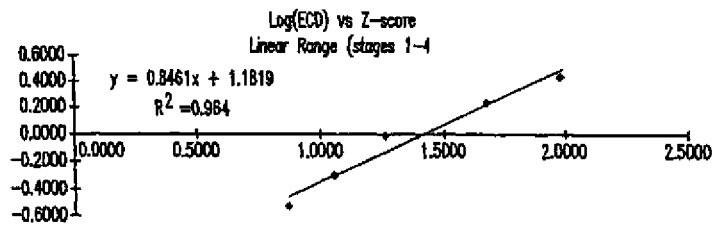
Figure 9:
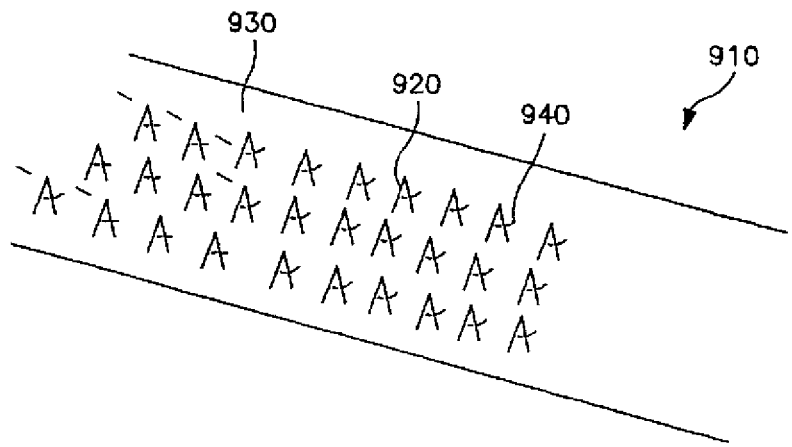

Particle Size Measurements:

Aerodynamic particle sizes of aerosol are summarized in the charts and graphs of FIGS. 8A-8C. Significant mass was deposited to the filter (0.2 μm cut off). MMAD was calculated to be 0.23 μm with a GSD of 5.34.

It will be understood that various details of the presently disclosed subject matter may be changed without departing from the scope of the subject matter. Furthermore, the foregoing description is for the purpose of illustration only, and not for the purpose of limitation.

What is claimed is:

1. An aerosol generation device, comprising:
   a. a heatable filament; and
   b. a composition coating the filament comprising a vaporizable carrier and a therapeutic agent;
      wherein when the filament is heated to at least the vaporization point of the carrier, the carrier vaporizes to release the therapeutic agent from the composition and upon cooling, the carrier condenses to thereby form an aerosol comprising the therapeutic agent and the carrier.

2. The aerosol generation device of claim 1, wherein the heatable filament is comprised of a coiled metal, a coiled semi-conductive material, a coiled ceramic material, a coiled thermo-electric polymer, or a combination thereof.

3. The aerosol generation device of claim 2, wherein the heatable coiled filament is comprised of a metal selected from the group consisting of nickel chrome, tungsten, stainless steel, aluminum, and titanium.

4. The aerosol generation device of claim 2, wherein the aerosol generation device further comprises a power source for applying an electrical current to the heatable coiled filament.

5. The aerosol generation device of claim 1, wherein the heatable filament comprises a plurality of heatable filaments.

6. The aerosol generation device of claim 5, wherein the plurality of filaments are arranged in parallel relation to one another and are affixed at an end to a substrate.

7. The aerosol generation device of claim 1, wherein the composition further comprises a co-solvent.

8. The aerosol generation device of claim 7, wherein the co-solvent is selected from the group consisting of an alcohol, an aldehyde, a ketone, dimethyl sulfoxide, water, and combinations thereof.

9. The aerosol generation device of claim 1, wherein the therapeutic agent forms a coating over at least a portion of an outer layer of the carrier.

10. The aerosol generation device of claim 1, wherein the therapeutic agent and the carrier are intermixed in the composition.

11. The aerosol generation device of claim 1, wherein the carrier is selected from the group consisting of capric acid, lauric acid, oleic acid, palmitic acid, stearic acid, phosphatidyl cholines (PC), polyethylene glycol (PEG), polyvinylpyrrolidone, lysine, leucine, polylysine, polyleucine, and combinations thereof.

12. The aerosol generation device of claim 1, wherein the therapeutic agent comprises a small molecule, a polynucleotide, a polypeptide, or a recombinant virus.

13. The aerosol generation device of claim 12, wherein the therapeutic agent comprises a polynucleotide encoding a cystic fibrosis transmembrane conductance regulator polypeptide.

14. The aerosol generation device of claim 12, wherein the therapeutic agent comprises a recombinant virus comprising a polynucleotide encoding a cystic fibrosis transmembrane conductance regulator polypeptide.

15. A metered dose inhaler comprising the aerosol generation device of claim 1 for use in pulmonary delivery of the therapeutic agent to a subject.

16. A rodent nose-only exposure chamber comprising the aerosol generation device of claim 1 for use in pulmonary delivery of the therapeutic agent to a rodent subject.

17. The exposure chamber of claim 16, further comprising an elutriator positioned in flow communication between the aerosol generation device and the exposure chamber.

18. An aerosol generation device, comprising:
   a. a heating element having a surface; and
   b. a composition coating at least a portion of the heating element surface and comprising a carrier and a therapeutic agent;
      wherein when the heating element surface is heated to at least the vaporization point of the carrier, the carrier vaporizes to release the therapeutic agent from the composition and upon cooling, the carrier condenses around the therapeutic agent to thereby form an aerosol comprising the therapeutic agent and the carrier.

19. The aerosol generation device of claim 18, wherein the heating element comprises a heatable filament.

20. The aerosol generation device of claim 18, wherein the heatable filament is comprised of a coiled metal, a coiled semi-conductive material, a coiled ceramic material, a coiled thermo-electric polymer, or a combination thereof.

21. The aerosol generation device of claim 20, wherein the heatable filament is comprised of a metal selected from the group consisting of nickel chrome, tungsten, stainless steel, aluminum, and titanium.

22. The aerosol generation device of claim 19, wherein the aerosol generation device further comprises a power source for applying an electrical current to the heatable filament.

23. The aerosol generation device of claim 19, wherein the heatable filament comprises a plurality of heatable filaments.

24. The aerosol generation device of claim 23, wherein the plurality of filaments are arranged in parallel relation to one another and are affixed at an end to a substrate.

25. The aerosol generation device of claim 18, wherein the composition further comprises a co-solvent.

26. The aerosol generation device of claim 25, wherein the co-solvent is selected from the group consisting of an alcohol, an aldehyde, a ketone, dimethyl sulfoxide, water, and combinations thereof.

27. The aerosol generation device of claim 18, wherein the therapeutic agent forms a coating over at least a portion of an outer layer of the carrier.

28. The aerosol generation device of claim 18, wherein the therapeutic agent and the carrier are intermixed in the composition.

29. The aerosol generation device of claim 18, wherein the carrier has a vaporization temperature that is less than the vaporization temperature of the therapeutic agent.

30. The aerosol generation device of claim 18, wherein the carrier has a vaporization temperature that is less than 500° C.

31. The aerosol generation device of claim 18, wherein the carrier is selected from the group consisting of capric acid, lauric acid, oleic acid, palmitic acid, stearic acid, phosphatidyl cholines (PC), polyethylene glycol (PEG), polyvinylpyrrolidone, lysine, leucine, polylysine, polyleucine, and combinations thereof.

32. The aerosol generation device of claim 18, wherein the therapeutic agent comprises a small molecule, a polynucleotide, a polypeptide, or a recombinant virus.

33. The aerosol generation device of claim 32, wherein the therapeutic agent comprises a polynucleotide encoding a cystic fibrosis transmembrane conductance regulator polypeptide.

34. The aerosol generation device of claim 32, wherein the therapeutic agent comprises a recombinant virus comprising a polynucleotide encoding a cystic fibrosis transmembrane conductance regulator polypeptide.

35. A metered dose inhaler comprising the aerosol generation device of claim 18 for use in pulmonary delivery of the therapeutic agent to a subject.

36. A rodent nose-only exposure chamber comprising the aerosol generation device of claim 18 for use in pulmonary delivery of the therapeutic agent to a rodent subject.

37. The exposure chamber of claim 36, further comprising an elutriator positioned in flow communication between the aerosol generation device and the exposure chamber.

38. A method of producing an aerosol, comprising:
 a. providing an aerosol generation device comprising:
  i. a heating element having a surface; and
  ii. a composition coating at least a portion of the heating element surface, the composition comprising a carrier and a therapeutic agent;
 b. heating the surface of the heating element to vaporize the carrier and produce a heated vapor of the carrier and the therapeutic agent, thereby propelling the therapeutic agent from the surface of the heating element; and
 c. cooling the vapor to condense the carrier and the therapeutic agent compound into an aerosol.

39. The method of claim 38, wherein the heating element comprises a heatable filament.

40. The method of claim 39, wherein the heatable filament is comprised of a coiled metal, a coiled semi-conductive material, a coiled ceramic material, a coiled thermo-electric polymer, or a combination thereof.

41. The method of claim 40, wherein the heatable filament is comprised of a metal selected from the group consisting of nickel chrome, tungsten, stainless steel, aluminum, and titanium.

42. The method of claim 38, wherein the heatable filament comprises a plurality of heatable filaments.

43. The method of claim 38, wherein the composition further comprises a co-solvent.

44. The method of claim 43, wherein the co-solvent is selected from the group consisting of an alcohol, an aldehyde, a ketone, dimethyl sulfoxide, water, and combinations thereof.

45. The method of claim 38, wherein the therapeutic agent forms a coating over at least a portion of an outer layer of the carrier.

46. The method of claim 38, wherein the therapeutic agent and the carrier are intermixed in the composition.

47. The method of claim 38, wherein the carrier has a vaporization temperature that is less than the vaporization temperature of the therapeutic agent.

48. The method of claim 38, wherein the carrier has a vaporization temperature that is less than 500° C.

49. The method of claim 38, wherein the carrier is selected from the group consisting of capric acid, lauric acid, oleic acid, palmitic acid, stearic acid, phosphatidyl cholines (PC), polyethylene glycol (PEG), polyvinylpyrrolidone, lysine, leucine, polylysine, polyleucine and combinations thereof.

50. The method of claim 38, wherein the therapeutic agent comprises a small molecule, a polynucleotide, a polypeptide, or a recombinant virus.

51. The method of claim 50, wherein the therapeutic agent comprises a polynucleotide encoding a cystic fibrosis transmembrane conductance regulator polypeptide.

52. The method of claim 50, wherein the therapeutic agent comprises a recombinant virus comprising a polynucleotide encoding a cystic fibrosis transmembrane conductance regulator polypeptide.

53. The method of claim 38, wherein heating the surface of the heating element is by resistive heating of the heating element.

54. The method of claim 38, wherein heating the surface of the heating element is rapid.

55. The method of claim 38, wherein cooling the vapor is by exposure of the vapor to ambient air.

56. A method of administering a respiratory therapeutic agent to a subject comprising administering the aerosol of claim 38 to the subject.

* * * * *

UNITED STATES PATENT AND TRADEMARK OFFICE
CERTIFICATE OF CORRECTION

| | | |
|---|---|---|
| PATENT NO. | : 8,165,460 B2 | Page 1 of 7 |
| APPLICATION NO. | : 11/666367 | |
| DATED | : April 24, 2012 | |
| INVENTOR(S) | : Hickey et al. | |

It is certified that error appears in the above-identified patent and that said Letters Patent is hereby corrected as shown below:

Delete the title page and substitute therefore the attached title page showing the corrected illustrative figure and the corrected title.

On title page, item 54 and in the specification, Column 1, Title
add "SAME" after the last word "USING"

In the Drawings
Delete FIGS. 1-9 and substitute therefore the attached FIGS. 1-9.

Formal drawings are shown herein as originally submitted on March 11, 2008 and are to be incorporated with the issued patent.

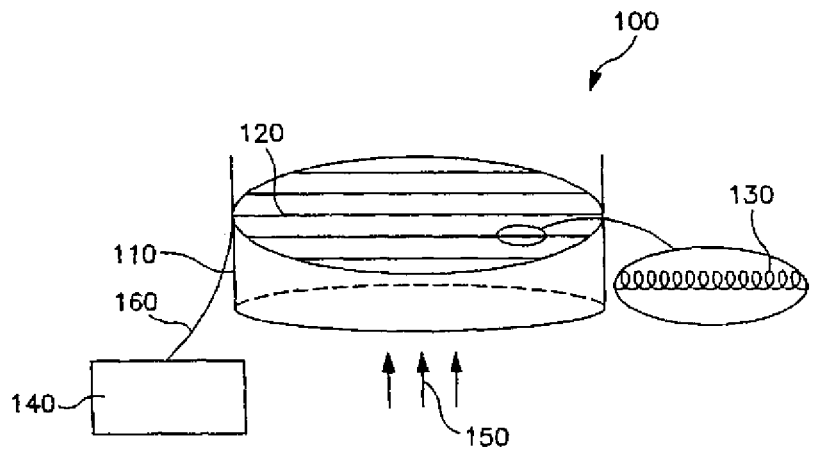

FIG. 1

Signed and Sealed this
Twenty-fourth Day of December, 2013

Margaret A. Focarino
*Commissioner for Patents of the United States Patent and Trademark Office*

Formal drawings are shown herein as originally submitted on March 11, 2008 and are to be incorporated with the issued patent.
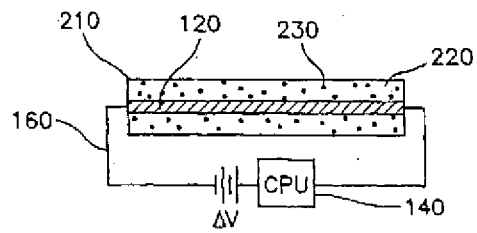
FIG. 2A
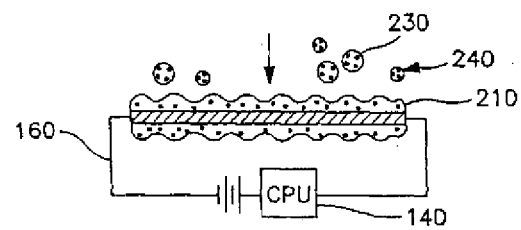
FIG. 2B
Formal drawings are shown herein as originally submitted on March 11, 2008 and are to be incorporated with the issued patent.
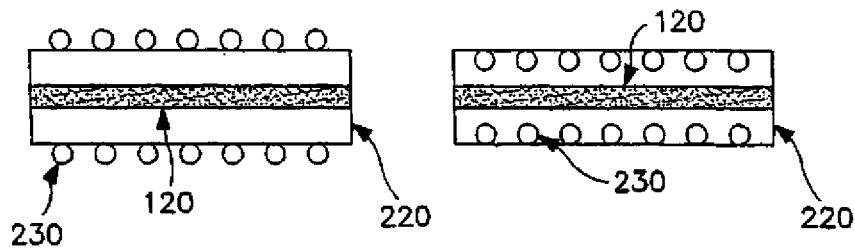
FIG. 3A  FIG. 3B

Formal drawings are shown herein as originally submitted on March 11, 2008 and are to be incorporated with the issued patent.

Formal drawings are shown herein as originally submitted on March 11, 2008 and are to be incorporated with the issued patent.

Formal drawings are shown herein as originally submitted on March 11, 2008 and are to be incorporated with the issued patent.

Formal drawings are shown herein as originally submitted on March 11, 2008 and are to be incorporated with the issued patent.

| Time (sec) | 2V | 4V | 6V |
|---|---|---|---|
| 0 | 25 | 25 | 25 |
| 5 | | | 42 |
| 10 | 42 | 50 | 80 |
| 15 | | | 110 |
| 20 | 50 | 82 | |
| 25 | | | |
| 30 | 64 | 110 | |
| 35 | | | |
| 40 | 74 | | |
| 45 | | | |
| 50 | 82 | | |
| 55 | | | |
| 60 | 88 | | |

Formal drawings are shown herein as originally submitted on March 11, 2008 and are to be incorporated with the issued patent.

Formal drawings are shown herein as originally submitted on March 11, 2008 and are to be incorporated with the issued patent.

Formal drawings are shown herein as originally submitted on March 11, 2008 and are to be incorporated with the issued patent.

Formal drawings are shown herein as originally submitted on March 11, 2008 and are to be incorporated with the issued patent.

(12) United States Patent
Hickey et al.

(10) Patent No.: US 8,165,460 B2
(45) Date of Patent: Apr. 24, 2012

(54) COATED FILAMENT FOR EVAPORATION/CONDENSATION AEROSOL GENERATION OF THERAPEUTIC AGENTS AND METHODS FOR USING SAME

(75) Inventors: Anthony J. Hickey, Chapel Hill, NC (US); Hugh D. C. Smyth, Albuquerque, NM (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 966 days.

(21) Appl. No.: 11/666,367

(22) PCT Filed: Oct. 26, 2005

(86) PCT No.: PCT/US2005/038713
§ 371 (c)(1),
(2), (4) Date: Apr. 18, 2008

(87) PCT Pub. No.: WO2006/047663
PCT Pub. Date: May 4, 2006

(65) Prior Publication Data
US 2008/0199161 A1   Aug. 21, 2008

Related U.S. Application Data

(60) Provisional application No. 60/622,256, filed on Oct. 26, 2004.

(51) Int. Cl.
*A01G 13/06* (2006.01)

(52) U.S. Cl. ........ 392/387; 392/386; 392/390; 239/135; 239/136; 239/13

(58) Field of Classification Search ............ 392/386, 392/387, 390; 239/13, 135, 136
See application file for complete search history.

(56) References Cited

U.S. PATENT DOCUMENTS

| | | | |
|---|---|---|---|
| 4,627,432 A | 12/1986 | Newell et al. | |
| 4,811,731 A | 3/1989 | Newell et al. | |
| 4,922,901 A * | 5/1990 | Brooks et al. | 128/203.26 |
| 5,743,251 A | 4/1998 | Howell et al. | |
| 5,823,178 A | 10/1998 | Lloyd et al. | |
| 2004/0091541 A1 | 5/2004 | Unger | |

OTHER PUBLICATIONS

International Search Report and Written Opinion dated May 16, 2006.
International Preliminary Report on Patentability dated May 10, 2007.

(Continued)

*Primary Examiner* — Thor Campbell
(74) *Attorney, Agent, or Firm* — Jenkins, Wilson, Taylor & Hunt, P.A.

(57) ABSTRACT

An apparatus for generating an aerosol of a therapeutic agent and methods of using the same are disclosed. The apparatus comprises a heating element having a surface and a composition coating at least a portion of the heating element surface. The composition comprises a carrier and a therapeutic agent, wherein when the heating element surface is heated to at least the vaporization point of the carrier, the carrier vaporizes and releases the therapeutic agent from the composition as an aerosol. The heating element can be a coiled filament. The therapeutic agent can be a small molecule, a polynucleotide, a polypeptide, or a recombinant virus. The apparatus can be incorporated into a delivery device, such as a metered dose inhaler or an exposure chamber.

56 Claims, 6 Drawing Sheets